United States Patent
Vicente et al.

(10) Patent No.: US 11,752,105 B2
(45) Date of Patent: Sep. 12, 2023

(54) SPRAY DRYING PROCESS WITH CONTINUOUS PREPARATION OF SPRAY SOLUTION

(71) Applicant: Hovione Scientia Limited, Cork (IE)

(72) Inventors: João Vicente, Lisbon (PT); Clara Sá Couto, Amadora (PT); Rui Ferreira, Leiria (PT); Marcio Temtem, Quinta do Conde (PT)

(73) Assignee: Hovione Scientia Limited, Cork (IE)

( * ) Notice: Subject to any disclaimer, the term of this patent is extended or adjusted under 35 U.S.C. 154(b) by 426 days.

(21) Appl. No.: 16/971,789

(22) PCT Filed: Feb. 22, 2019

(86) PCT No.: PCT/GB2019/050495
§ 371 (c)(1),
(2) Date: Aug. 21, 2020

(87) PCT Pub. No.: WO2019/162688
PCT Pub. Date: Aug. 29, 2019

(65) Prior Publication Data
US 2021/0077405 A1    Mar. 18, 2021

(30) Foreign Application Priority Data
Feb. 22, 2018  (PT) .......................................... 110585

(51) Int. Cl.
*A61K 9/16* (2006.01)
*F26B 5/00* (2006.01)

(52) U.S. Cl.
CPC .......... *A61K 9/1688* (2013.01); *A61K 9/1617* (2013.01); *A61K 9/1623* (2013.01);
(Continued)

(58) Field of Classification Search
CPC .... A61K 9/1688; A61K 9/1617; A61K 9/168; F26B 5/005
See application file for complete search history.

(56) References Cited

U.S. PATENT DOCUMENTS

| | | |
|---|---|---|
| 5,222,807 A | 6/1993 | Gaddis |
| 5,857,773 A | 1/1999 | Tammelin |

(Continued)

FOREIGN PATENT DOCUMENTS

| | | |
|---|---|---|
| PT | 110585 | 2/2018 |
| WO | 2010111132 A2 | 9/2010 |

(Continued)

OTHER PUBLICATIONS

Foreign communication from a related application—International Search Report and Written Opinion of PCT/GB2019/050495 dated May 22, 2019, 11 pages.

(Continued)

*Primary Examiner* — Carlos A Azpuru
(74) *Attorney, Agent, or Firm* — Conley Rose, P.C.; Rodney B. Carroll

(57) ABSTRACT

The present invention discloses a spray drying process characterized by continuous preparation and immediate spray drying of a solution comprising at least one active pharmaceutical ingredient and/or at least one excipient, and at least one solvent. The said active pharmaceutical ingredient(s) and solvent(s) are combined, alone or along with one or more excipients to form a first suspension. Said suspension is continuously fed to an intensifier pump that pushes said suspension through at least one micro-reaction chamber and/or at least one micro-channel where the suspension's solid(s) component(s) is(are) dissolved into said solvent(s) by means of high energy mixing I forced contact at micro, nano and molecular level to form a solution stream. The said solution stream is then immediately and continu- (Continued)

ously fed to the spray dryer through at least one atomization nozzle, drying said atomized stream to obtain solid particles and collecting said solid particles. Single component particles or multi-component particles, particulate amorphous solid dispersion and pharmaceutical compositions are also disclosed. The present invention also discloses amorphous solid dispersions obtained by the method of the invention as well as pharmaceutical compositions containing the same.

33 Claims, 4 Drawing Sheets

(52) U.S. Cl.
CPC .......... *A61K 9/1635* (2013.01); *A61K 9/1641* (2013.01); *A61K 9/1694* (2013.01); *F26B 5/005* (2013.01)

(56) References Cited

U.S. PATENT DOCUMENTS

| | | | |
|---|---|---|---|
| 6,221,332 | B1 | 4/2001 | Thumm et al. |
| 10,821,375 | B2 * | 11/2020 | Fonseca ............... B01D 63/088 |
| 2002/0071870 | A1 | 6/2002 | Sharma |
| 2005/0031692 | A1 | 2/2005 | Beyerinck et al. |
| 2009/0269250 | A1 | 10/2009 | Panagiotou et al. |
| 2014/0319071 | A1 | 10/2014 | Patel et al. |

FOREIGN PATENT DOCUMENTS

| | | | |
|---|---|---|---|
| WO | 2016156841 | * | 10/2016 |
| WO | 2016156841 | A1 | 10/2016 |
| WO | 2017/129988 | A1 * | 8/2017 |
| WO | 2017129988 | A1 | 8/2017 |
| WO | 2019162688 | A1 | 8/2019 |

OTHER PUBLICATIONS

Foreign communication from a related application—International Preliminary Report on Patentability of PCT/GB2019/050495 dated May 8, 2020, 16 pages.

Duarte, Iris, et al., "776b: Microfluidization as an Enabling Technology for Solubility Enhancement," AIChE Annual Meeting, Nov. 3, 2017, 4 pages, XP055587642.

* cited by examiner

SPRAY DRYING PROCESS WITH CONTINUOUS PREPARATION OF SPRAY SOLUTION

CROSS REFERENCE TO RELATED APPLICATIONS

This application is a filing under 35 U.S.C. 371 of International Application No. PCT/GB2019/050495 filed Feb. 22, 2019, entitled "A Spray Drying Process with Continuous Preparation of Spray Solution," which claims priority to Portuguese Patent Application No. 110585 filed Feb. 22, 2018, both of which are incorporated by reference herein in their entirety.

FIELD OF INVENTION

The present invention is in the technical field of processes for manufacturing single component particles, multi-component particles in amorphous or crystalline form and amorphous solid dispersions having particle sizes in the micro- and/or nano-range. More particularly, the present invention relates to a spray drying process wherein the spray solution is prepared in a continuous mode and continuously fed to the spray dryer. The invention also relates to a process for preparing a spray solution continuously using an apparatus that improves dissolution kinetics, solubility and stability of the particles in a solvent system. The process can be applied in the field of pharmaceuticals, particularly in the processing of active pharmaceutical ingredients (APIs), intermediate drug product or drug products. The process is designed to allow the manufacturing and particle engineering of particulate solid dispersions in a single manufacturing step eliminating the spray solution hold time prior to spray drying.

BACKGROUND OF THE INVENTION

Currently an increasing number of low solubility (which often translate into low bioavailability) drug candidates can be seen in the pharmaceutical research pipelines. In this context, amorphous solid dispersions have emerged as an enabling drug release platform since they can promote drug supersaturation in the site of absorption. Amongst other technologies, spray drying process is increasingly popular for the manufacture of amorphous solid dispersions.

The process of producing spray dried pharmaceutical products generally comprises two main discontinuous steps: (i) preparing a spray solution and (ii) spray drying the solution. First, the spray solution is prepared in a stirred tank by dissolving at least one active pharmaceutical ingredient in one or more aqueous or non-aqueous solvents alone or along with one or more excipients. After the complete dissolution of the solids is achieved in the stirred tank, the spray solution is fed through an atomization nozzle to a spray drying chamber where the solvent is evaporated from the fine droplets by the hot drying gas to produce solid particulates.

Often, the active pharmaceutical ingredients and/or the excipients have low dissolution kinetics in the aqueous or non-aqueous solvent(s), requiring many hours to achieve complete dissolution when using conventional methods/apparatus, such as, a stirred tank to prepare the spray solution. Also, the capacity of the feed tank can be particularly limiting in the case of low solubility active pharmaceutical ingredients. In these cases very low concentrated/high volume spray solutions may be compulsory, requiring manufacture of multiple batches of spray solution. Additionally, many active pharmaceutical ingredients (APIs) and excipients have a low stability while in solution, making the preparation of spray solutions in batch mode (with inherent hold times) an unsuitable method due to chemical degradation. This is particularly relevant in cases where the active pharmaceutical ingredients or excipients show poor dissolution kinetics and low solubility.

In summary, the low dissolution kinetics, feed tank inadequate capacity, and low stability/solubility properties of the active pharmaceutical ingredients and excipients may make the spray solution preparation in batch mode (e.g. in stirred tank) unfeasible for the manufacture of pharmaceutical spray dried products.

Active pharmaceutical ingredients and excipients having low dissolution kinetics are usually milled to decrease the particle size and thus increase the surface area available for mass transfer from the solid to the liquid phase. As a result of the higher surface area the time required for dissolution is decreased. The current art comprises several techniques to reduce particle size, such as jet milling, high shear mixing and ball milling methods. Even though these techniques are often effective they imply at least one additional and discontinuous step in the preparation of the spray solution.

Another common issue when preparing large batches of the spray solution is the failure to completely dissolve the drug substance and/or excipients in the process solvent within a reasonable amount of time. This is the case with respect to drug substances with low dissolution kinetics or if the polymeric excipients are not well dispersed. In the case of polymeric excipients, the polymer may clump forming a diffusion limiting gel layer on the polymer-solvent interface which impairs dissolution kinetics.

In addition many active pharmaceutical ingredients show low stability in solution and tend to degrade over time. As a result the purity of the spray dried material may be lower for the latter sprayed fractions of solution, raising homogeneity issues as the spray dried product does not have the same dosage throughout the batch.

The state-of-the-art includes a number of examples for preparing particles of drugs having low solubility and dissolution kinetics.

For example, US 2005/0031692 relates to a process for preparing a spray solution by dissolving a low solubility drug and a polymer. This document relates to a discontinuous method of preparing a spray solution. US 2014/0319071 also relates to a discontinuous process in which a system for polymer dissolution is used.

U.S. Pat. No. 5,222,807 relates to a continuous low shear solids dissolution system only for polymer dissolution using a low shear mix. Also, in U.S. Pat. No. 5,857,773 a pressure pump is used to accelerate a mixture of polymer and solution through static mixers for dissolution of compounds under pressure.

WO 2010/111132 relates to a spray drying process, where the spray solution, although through a discontinuous process, is formed by a feed suspension at a temperature T1 that is passed through a heat exchanger increasing the temperature to T2 using external energy input. The solid components in the feed suspension solubilize due to the temperature effect, forming the spray solution. For many spray solutions the increase in temperature may be appropriate for increasing the solids solubility, but this is not sufficient for improving significantly the dissolution kinetics. In order to improve dissolution kinetics, solids size reduction is typically required, preferably along with temperature increase in order to promote the diffusion of solids into the liquid phase.

WO 2016156841 describes a method to continuously manufacture micro and/or nanoparticles comprising the steps of preparing a first solution comprising at least one component and at least one solvent and a second solution comprising at least one anti-solvent of at least one component comprised in the first solution. The first solution and the second solution are fed to a micro-reactor and are mixed by means of micro-fluidization to produce a suspension by precipitation or co-precipitation. The suspension is then fed to a filtration system to increase the solids concentration. The solid particles from the suspension are then isolated by spray-drying. More specifically, in the method of WO 2016156841 a micro-reaction technology is used to control precipitation of the particles during the manufacturing the process.

US 2009/0269250 and U.S. Pat. No. 6,221,332 relate to a system for continuously processing at least two liquid feed streams through an intensifier pump and micro-reactors.

In summary, the state-of-the-art only discloses strategies for preparing spray solutions and particulate materials of low soluble drugs. However, none of the methods disclosed in the state-of-the-art addresses problems associated with respect to hold time between solution preparation and spray drying, low dissolution kinetics, feed tank inadequate capacity, low stability/solubility properties of the active pharmaceutical ingredients or excipients and batch mode methods.

The inventors of the present invention have appreciated that there is a need for a process and a system that effectively overcomes the problems indicated above.

Thus, the aim of the present invention is to solve the problem of solubilizing active pharmaceutical ingredients and/or excipients with low solubility and/or low dissolution kinetics and/or low stability in solution. More specifically, the present invention aims to provide a method for solubilizing active pharmaceutical ingredients and/or excipients continuously in one single step operation encompassing particle size reduction, heat generation and homogeneous mixing of the spray solution. All these phenomena increase the dissolution kinetics and solids solubility in the continuous spray solution preparation. With the present invention a more efficient process is achieved as no additional batch operation is required to prepare the spray solution. The inventors of the present invention have designed a process and a system in which both the spray solution preparation and the spray drying step can be performed continuously and simultaneously. In addition, the present invention provides a process and a system in which batch size is not limited by the feed tank capacity and no hold time between solution preparation and spray drying is required eliminating potential spray solution stability issues.

The present invention also aims to provide a process wherein the spray solution is prepared in a continuous mode and continuously fed to a spray dryer using an apparatus that improves dissolution kinetics and/or solubility in a solvent system through a high energy mixing or forced contact of the spray solution components at micro, nano and molecular level within a defined micro-reaction chamber and/or micro-channel. The high energy phenomena used in the micro-reaction chamber and/or micro-channel cause simultaneously micronization of the solids, local heat generation, and homogeneous mixing of all components promoting faster dissolution kinetics and enhanced solubility in the solvent(s) system.

SUMMARY OF THE INVENTION

According to the present invention there is provided a process for the continuous manufacture of single component particles and/or multi-component particles comprising the steps of:

- continuously feeding a suspension comprising at least one component and at least one solvent to at least one microfluidization device;
- mixing the suspension in the microfluidization device by means of micro-reaction or microfluidization to produce a homogeneous spray solution;
- feeding said spray solution in a continuous mode to a spray dryer;
- atomizing said spray solution to produce droplets using at least one atomization nozzle; and
- drying said droplets in a drying chamber to obtain particles.

Preferably, the suspension is prepared by mixing in a continuous or discontinuous mode a solution comprising at least one component with a solution comprising at least one solvent. The at least one component may comprise at least one active pharmaceutical ingredient (API) alone, or in combination with at least one excipient. Preferably, the active pharmaceutical ingredient has low solubility, dissolution kinetics or poor stability in solution. Preferably, single component particles and/or multi-component particles comprises amorphous solid dispersions. Preferably, the microfluidization is effected using at least one microreactor and/or at least one micro-chamber, which may be a continuous flow reactor. Preferably, the microfluidization device operates in a recirculation mode. The suspension comprising the active component and the solvent is preferably fed to the microreactor/microchannel using at least one intensifier pump, at a preferred pressure range of about 1 bar to about 3500 bar, optionally in the range of about from 1 to about 2000 bar.

Preferably, the suspension comprising the active component and the solvent is mixed in the one or more channels of microreactor/microchannel such that the particle size of the active component is reduced by micronization and heat is generated.

According to another aspect of the present invention there is provided a system for continuous manufacture of single component particles and/or multi-component particles comprising:

- a microfluidizer for mixing a suspension comprising at least one component and at least one solvent by means of micro-reaction or microfluidization to produce a homogeneous spray solution;
- means for continuously feeding the suspension to the microfluidizer, which preferably comprises at least one microreactor and/or at least one micro-chamber; and
- a spray dryer comprising at least one atomization for atomizing said spray solution to produce droplets and a drying chamber for drying said droplets to obtain particles.

According to another aspect of the present invention there is provided a process for manufacturing single component particles and/or multi-component particles using the system according to the present invention. Preferably, the single component particles or multi-component particles comprises amorphous solid dispersions or particulate amorphous dispersion.

According to another aspect of the present invention there is provided single component particles or multi-component particles or a particulate amorphous dispersion obtainable by the process of the present invention for use in increasing the bioavailability of the API.

Other aspect of the invention relates to single component particles, multicomponent particles and particulate amorphous solid dispersions obtainable by the method of the present invention, and pharmaceutical compositions comprising said single component particles, multicomponent particles and particulate amorphous solid dispersions.

The term "solid" is defined as a solid or mixture of solids, comprising at least one active pharmaceutical ingredient and/or at least one excipient.

The term "amorphous solid dispersion" is defined as the dispersion of at least one API in a matrix, in the amorphous state. The matrix may comprise crystalline or amorphous polymers, surfactants or mixtures thereof.

The term "API-only" is defined as particles comprising at least one API in the absence of excipients.

The term "excipient" is defined as a substance that serves as the vehicle or medium for a drug or other active substance.

The term "solvent" according to the present invention is a solvent or mixture of solvents wherein the solids, e.g. active pharmaceutical ingredient, and, if applicable, the excipient or excipients of interest, are soluble.

The term "suspension" according to the present invention is a mixture of the "solid" stream and "solvent" stream wherein the solid is not fully solubilized in the solvent.

The term "microreaction" refers to a technology that involves physical and/or chemical reactions within microreactors, micromixers, microchannels or any other component comprised within the field. The term "microfluidization" encompasses continuous fluid processing through these microchannels, involving high shear, cavitation and uniform mixing in the meso- and micromixing range. Preferably, in the case of multicomponent particles, the proportion of at least one active pharmaceutical ingredient to one or more than one excipient ranges from 95% to 5% (w/w) to 5% to 95% (w/w).

The term "single component particles" refers to particles containing a single component or substance, e.g. active pharmaceutical ingredient, excipient.

The term "multi-component particles" refers to particles containing a mixture of several components or substances e.g. active pharmaceutical ingredient, excipient.

The foregoing and other features and advantages of the invention will be more readily understood upon consideration of the following detailed description of the invention, and the accompanying drawings.

DETAILED DESCRIPTION OF THE INVENTION

The present invention discloses a continuous spray drying method characterized by continuous preparation and spray drying of a spray solution comprising at least one active pharmaceutical ingredient or at least one excipients or a combination of one or more APIs and excipients, and at least one solvent.

Figure 2A:
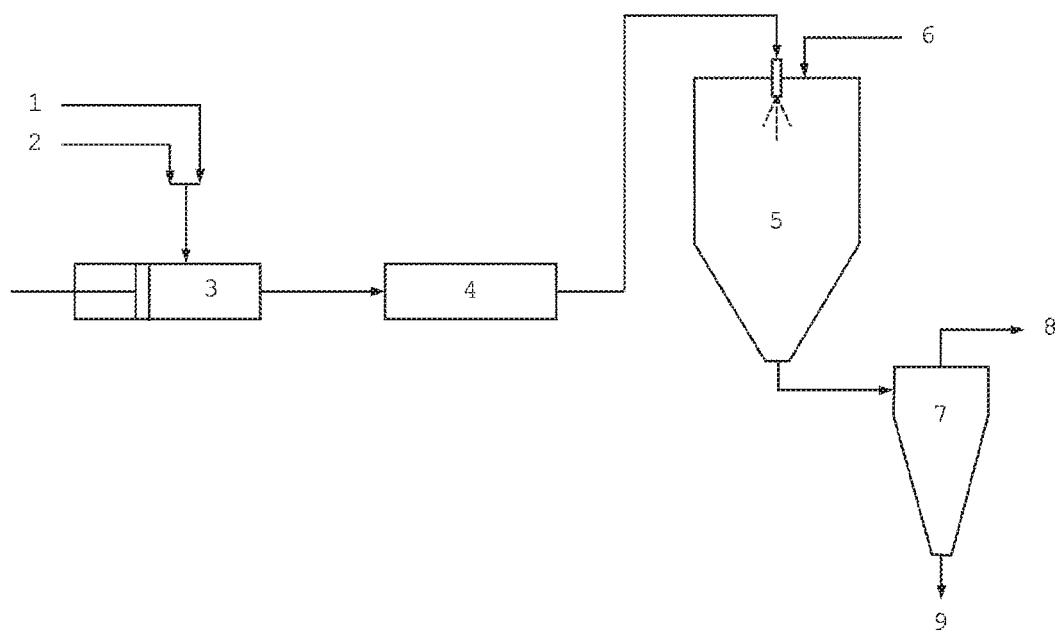
FIG. 2A is a schematic representation of an embodiment of the system of the present invention.

Referring now to the invention in more detail, in FIG. 2A it is shown a system comprising an optional buffer tank which receives at least one solvent stream (1) and at least one solid stream (2); a pump (3); a microfluidization apparatus/device (4); an optional buffer tank; a spray dryer comprising a drying camber (5) and means for recovering the dried particles (7).

Preferably, the solvent stream (1) and the solid stream (2) are fed to a buffer tank (2) and combined either discontinuously or continuously, preferably at individually controlled rates to form a suspension.

Preferably, the buffer tank is connected to a pump (3) which may in turn be connected to the microfluidization apparatus (4). The pump (3) comprises an intensifier pump or any pump known to a person skilled in the art suitable for pumping the suspension in the buffer tank at pressure sufficient to continuously transport the suspension to the microfluidization apparatus (4).

Preferably, the microfluidization apparatus (4) comprises one or more microreactors and/or micro-channels. Preferably, the microfluidization apparatus (4) is operated in a recirculation mode.

Preferably, the reaction chamber in the micro-reactor comprises one or more channels of well-defined diameter and size. Preferably, the diameter of the channels is the range of about 10 to about 1000 um or about 10 micron to about 400 microns. More preferably, the diameter is in the range of about 50 microns to about 200 microns. The microchannels may also have a diameter ranging from 1 to 10 um or 1 to 5 um.

The number of micro-channels and/or micro-reactors used in the present invention is not limited, but preferably ranges from 1 to 10. In embodiments using more than one micro-reactor, the micro-reactors may be arranged in series or in parallel.

The microfluidization apparatus facilitates further mixing and micronization of the particles in the suspension to form a homogenous spray solution. The microfluidization apparatus also facilitates heat generation or increase in temperature which increases the solubility of the solids in the suspension.

The microfluidization apparatus is connected to a spray drying unit (5). Preferably, the microfluidization apparatus is connected to the spray drying unit (5) via a buffer tank.

Preferably, a buffer tank is used to discharge the homogenous spray solution from the microfluidization apparatus prior to being fed to the spray dryer (5).

Preferably, an intensifier pump is used to continuously transport the spray solution from the buffer tank or the microfluidization apparatus to an atomizer in the spray dryer for drying and separating the solid particles.

Preferably, the microfluidization apparatus operates in a recirculation mode. The microfluidization apparatus may be connected to the buffer tank in which the at least one component and the at least one solvent are combined, to recirculate the solution from microfluidization apparatus until the desired solids dissolution is achieved. Preferably, the system provides a second buffer tank connected to the first buffer tank for receiving multiple batches of solution from the first buffer tank in a semi-continuous mode, such that the solution from the second buffer tank is continuously fed to the spray dryer.

In an embodiment of the present invention, a spray drying unit is used for drying and recovering the solid material from the suspension. The spray drying unit may be any suitable spray drying device known in the art. Preferably, the spray drying apparatus comprises a spray drying chamber (5) where the solution from the microfluidization apparatus (4)

in the form of a liquid stream is continuously fed using an atomization nozzle to form droplets and dried with drying gas (6).

The spray drying apparatus also comprises means for recovering the dried particles from the spray dryer chamber. In FIG. 2A, the dried particles are separated from the drying gas in a cyclone (7) and collected in an outlet stream (9), while the drying gas exits the cyclone (7) in an outlet stream (8). However, the means for recovering dried particles from the spray dryer chamber may also take the form of other means, which will be known to the person skilled in the art, such as a filter bag.

Figure 1A:
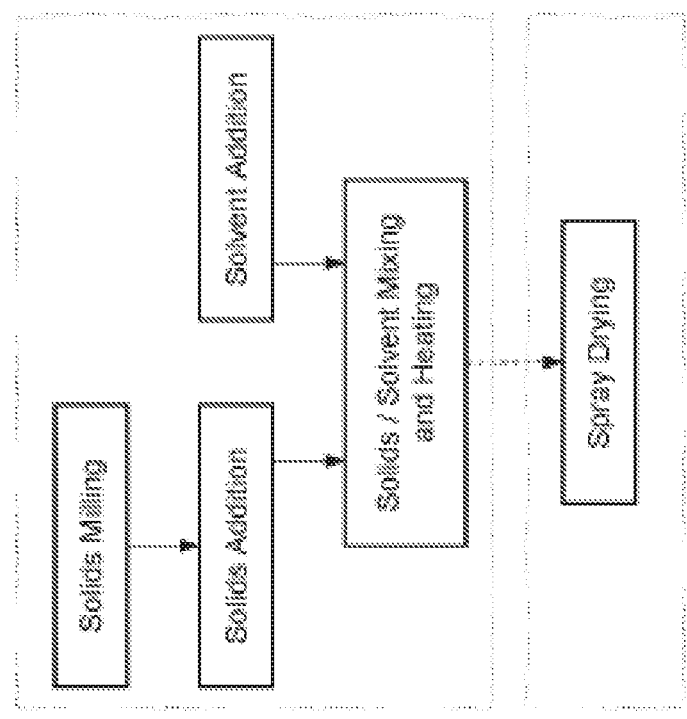
FIG. 1A shows a schematic representation of the process steps as per the state-of-the-art.
Figure 1B:
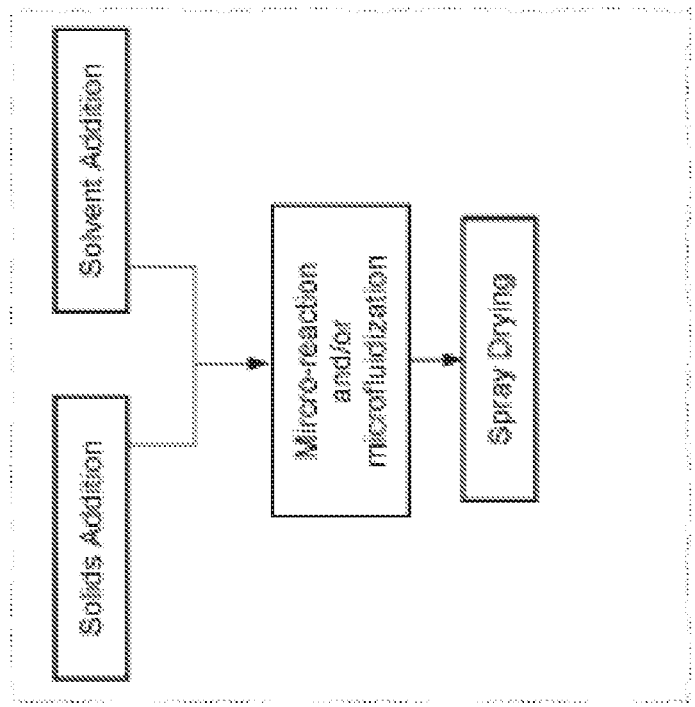
FIG. 1B shows a schematic representation of the process steps as per the present invention disclosure.

FIG. 1A shows a diagram of the method of prior art. In the state of the art the spray solution is prepared by first milling the solids (APIs) in a discontinuous process and then a stream of the milled solids and a stream of solvent are fed to a stirred tank in which the solids are dissolved in the solvent by stirring and mixing over a period of time. If needed, heat from the external source may also be applied during the mixing step. The resulting suspension is then subjected to a spray drying process to obtain solids particles. FIG. 1B shows a diagram of the method of the present invention In a preferred embodiment of the present invention, a stream comprising at least one solvent (1) and a stream comprising at least one solids (2) are combined discontinuously or continuously at individually controlled rates to form a suspension. Preferably, the stream comprising the solids and the stream comprising the solvent are fed to a buffer tank. In a preferred embodiment, the mixing of solvent stream and solid stream occurs under controlled conditions in order to promote dispersion of the solid stream into the solvent stream. Preferably, a buffer and/or a static mixer are used to combine the solid and solvent stream to form the suspension. Preferably, the solid and solvent stream are combined at a ratio at which the solid is within the solubility limit in the solvent system and is in the range of, but not limited to, about 1% to about 50% (w/w) or about 5% to about 15%. The ratio between solvent and solid may also be optimized to control particle characteristics after spray drying (e.g. particle size and density).

Preferably, the suspension is continuously fed to one or more intensifier pumps (3) at a controlled rate which depends for example on the characteristics of the suspension. Then, the suspension is pressurized with the one or more intensifier pumps (3) to one or more micro-reactor (4), causing the components of the suspension to interact at micro, nano and molecular level resulting in a homogeneous spray solution. The microreactor facilitates highly effective molecular contact/interaction of the components of the suspension within a defined reaction chamber and/or micro channel, resulting in solids micronization and high energy mixing which ultimately results in improved dissolution kinetics and solubility.

Preferably, the suspension comprises of at least one solvent, at least one active pharmaceutical ingredient and/or at least one excipient. Preferably, the least one active pharmaceutical ingredient and/or the excipient has poor stability in solution, low solubility and/or low dissolution kinetics properties.

In a preferred embodiment, the process pressure and solids concentration in the suspension can be optimized to promote micro-reaction such that the dissolution of the solids in the suspension is increased.

In a preferred embodiment, the suspension is fed to the microreactor/microchannel at a pressure sufficient to form a homogenous spray solution.

The pressure may be in the range of from about 1 bar to about 3500 bar, preferably from about 20 to about 3500 bar, more preferably from about 100 to about 3000 bar, or from about 300 bar to about 2500 bar. Preferably, the pressure may also be in the range of from about 1 bar to about 2000 bar or 10 to 1500 bar.

It is also disclosed that during the mixing step in the micro-reactor the suspension, is preferably fed at a temperature Tin, may experience a temperature increase up to Tout as a result of the high energy interactions. The difference between Tin and Tout depends on the operating conditions and on the properties of the suspension stream. Preferably, the solids are soluble in the solvent within the range comprised between Tin and Tout. Tin and Tout may be controlled by external energy input to control degradation, solubility and dissolution kinetics.

The temperature Tin may be in the range of from about −10° C. to 100° C., preferably in the range of −5° C. to 80° C.

The temperature Tout may be in the range of from about 0° C. and 150° C., preferably in the range of 5° C. to 130° C.

Preferably, the spray suspension is pumped into a series of micro-reactors/micro-channels having at least about 1 to 10 micro-reactors or micro-channels.

Preferably, the homogenous spray solution formed in the microreactor is continuously fed to a spray dryer using a pump such as an intensifier pump or any pump suitable for transporting the spray solution to the spray dryer (5).

Preferably, the spray solution from the micro-reactor or microfluidization apparatus is immediately and continuously fed to the spray dryer.

Preferably, a buffer tank is used to discharge, continuously or discontinuously, the homogenous spray solution prior to being fed to the spray dryer (5). An intensifier pump may be used to transport the spray solution to the atomizer of the spray dryer.

In a preferred embodiment, connecting means/apparatus are provided for connecting the micro-reactors or micro-channels to a buffer tank, which in turn is connected to a spray drying apparatus.

Figure 2B:
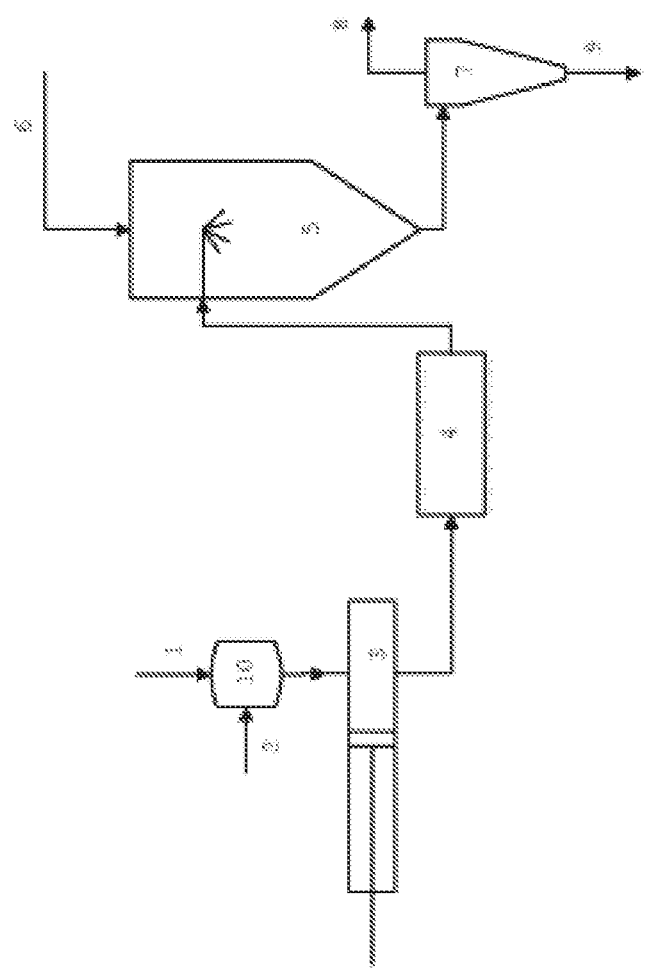
FIG. 2B is a schematic representation of an embodiment of the system of the present invention.

In a preferred embodiment, FIG. 2B shows means or an apparatus having a solvent stream (1) and solid stream (2) which are connected to a buffer tank (10), which in turn may be connected to an intensifier pump (3). The intensifier pump (3) is connected to micro-reactors/micro-channels (4) and these components (i.e. the unit comprising the apparatus comprising solvent and solid streams, buffer tank, pump and microreactor) are connected to a spray drying apparatus (5).

Figure 2C:
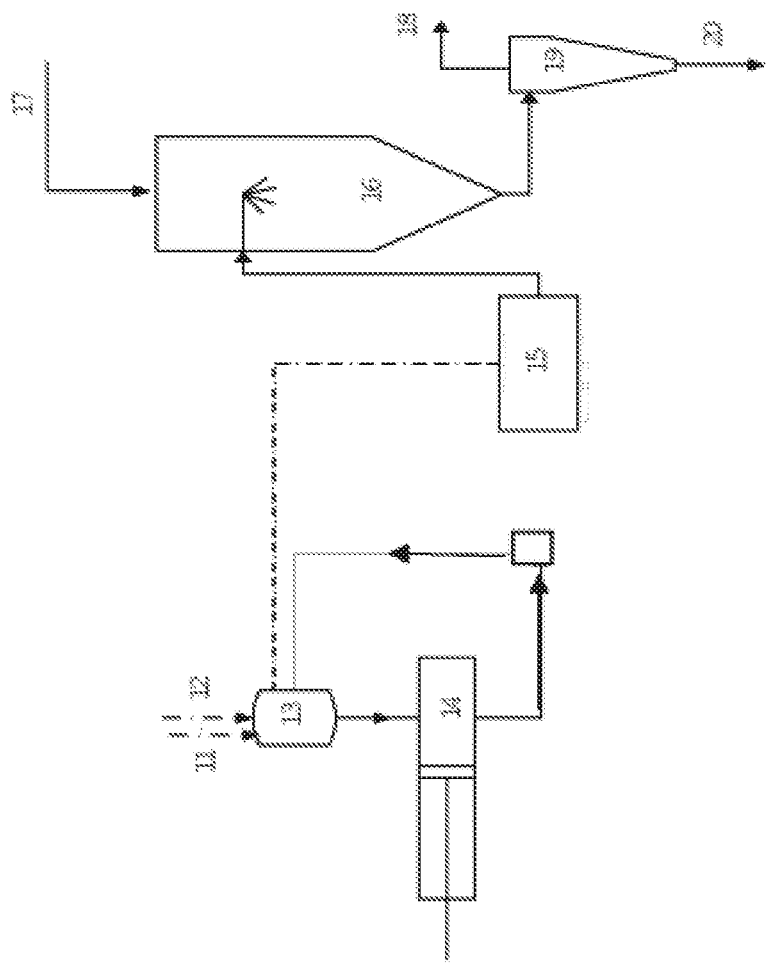
FIG. 2C is a schematic representation of an embodiment of the system of the present invention.

In another preferred embodiment, FIG. 2C shows a solids stream (11) and a solvent stream (12) being discharged into a first buffer tank (13), continuously or discontinuously. The solution or suspension comprising the solids and solvent in the buffer tank (13) is transported to micro-reactors/micro-channels (not shown), preferably using an intensifier pump (14). The solution or the suspension from the micro-reactors/micro-channels may be recirculated back to the buffer tank (12) until the desired solids dissolution is achieved. In a semi-continuous mode the solution from the buffer tank (12) may be transferred to a second buffer tank (15) which in turn is connected to a spray drying apparatus comprising a spray drying chamber (16). Preferably, in a semi-continuous mode multiple batches of the solution can be prepared in the first buffer tank (13). The multiple batches of solution in the first buffer tank (13) may be transferred to the second buffer tank (15), continuously or discontinuously, such that the solution is not exhausted in the second buffer tank (15), while the spray drying process is operating in a continuous mode. Preferably, the solution from the second buffer tank (15) is continuously fed to a spray drying chamber (16) using an atomization nozzle to form droplets and dried with drying gas (17). The spray drying apparatus also comprises means (19) for recovering the dried particles (20) from the spray dryer chamber (16), while the drying gas exits in an outlet stream (18).

In the present invention it is also disclosed that the spray solution is continuously fed to at least one atomizer that atomizes the spray solution into droplets inside a drying chamber (5) where the solvent is evaporated by the effect of a drying gas, forming a spray dried particles stream (9) that is collected on a cyclone or filter bag (7) installed at the outlet of the drying chamber (5).

Atomization can be promoted using specific types of atomizers such as, but not limited to, rotary nozzles, pressure nozzles, two fluid nozzles, ultrasonic nozzles or any other device capable of atomizing a solution, or preferentially, any device capable of forming droplets from a solution. Preferably, the atomization conditions and spray drying process parameters can be optimized to manufacture the desired particles. More preferably, a pressure nozzle is used, which is capable of atomizing the spray solution at hydrodynamic pressures ranging from about 1 to about 200 bar or about 10 to about 100 bar. The droplets formed in the present invention are preferably in the range of from about 1 micron to about 1000 micron, preferably between 1 micron to 200 microns, preferably between 30 microns to 200 microns or 30 microns to 80 microns.

The spray solution that is continuously fed through the atomizer to the spray drying chamber may comprise at least one dissolved active pharmaceutical ingredient and at least one solvent, alone or along with one or more excipients.

More specifically, the excipient(s) may be selected from the group comprising: polymers, surfactants, surface modifiers, sugars, amino acids, polysaccharides, for example, a cellulosic polysaccharide or derivative/cellulose-based polymers, chitin and chitosan, alginates or other polymer groups such as vinyl polymers, for example poly vinyl pirrolidone, or polymers with acrylic groups for example poly methyl acrylic, and any other polymer and combinations thereof.

The solvent used in preparing the spray solution may be selected from the group comprising: water, methanol, ethanol, propanol, acetone, butanone, tetrahydrofuran, dichloromethane, hexane, ethyl acetate, n-heptane, other organic solvents and combinations thereof.

Preferably, a pH adjusting agent such as sodium hydroxide, hydrochloric acid, tris buffer or citrate, acetate, lactate, meglumine, or the like is added to the "solvent" solution. Preferably, the temperature of the solvent may be adjusted. Preferably, the temperature is adjusted in the range of about −20 to 70° C. However, based on the substance or component which is dispersed in the solvent, a person skilled in the art can adjust the temperature suitably.

Preferably, the atomization conditions and spray drying process parameters can be optimized to manufacture the desired particles.

Preferably, the drying gas stream (6) comprises air, nitrogen or carbon-di-oxide. Preferably the drying gas is fed at a flow rate and at a temperature that are sufficient to evaporate the solvent(s) from the atomized spray solution up to an extent that solid particles are formed. Preferably, the drying gas flow rate ranges from 0.1 kg/h to 5000 kg/h, more preferably the drying gas flow rate ranges from 1 kg/h to 2000 kg/h. Preferably, the drying gas temperature ranges from about −20° C. to about 200° C., more preferably in the range of from −10° C. to 100° C. The drying gas can be recycled through a condenser unit to condensate most of the solvent. The condensed liquid is then pumped and the gas is heated to temperatures ranging from about −20° C. to about 200° C. before re-entering the drying chamber. The condenser unit typically operates at temperatures ranging from about −20° C. to about 30° C.

The spray drying chamber (7) has enough volume to allow the contact between the atomized spray solution and the drying gas being fed at individually controlled flow rates. Preferably, the spray drying chamber has enough volume to allow the contact between the atomized spray solution and the drying gas and to allow the evaporation of the solvent(s) from the atomized spray solution up to an extent that solid particles are formed.

Preferably, the spray dried material is further dried in a secondary drying discontinuous operation using at least one of the following means: by reducing pressure below room pressure, heating above room temperature or by agitation.

In the present invention, spray solutions are prepared using high shear mixing in the apparatus such as in microchannels and/or micro-reactors. Such high shear mixing allows for faster dissolution kinetics and enhanced solubility as a result of increased surface area of the drugs and/or excipients particles by particle size reduction and local heat generation of the spray solution which spontaneously increases the temperature.

Furthermore, in the process of the present invention, microfluidization is effected by using an apparatus such as micro-channels and/or micro-reactors to promote micronization and to improve solids dissolution kinetics and solubility. In the present invention a suspension comprising at least one solid component and at least one solvent may be micronized by microfluidization in order to obtain a homogeneous spray solution. The resulting homogeneous spray solution may then be spray dried to remove the solvents resulting in solid particles.

In a preferred embodiment of the present invention only one stream of a suspension comprising at least one solid component and at least one solvent is used for preparing a spray solution. The single stream of suspension is continuously fed to a micro reactor and then to a spray-dryer to obtain solid material particles.

Furthermore, in a preferred embodiment of the present invention, there is no need for a filtration system for concentrating the spray solution obtained from the micro reactor prior to feeding the solution to a spray dryer. Also, in a preferred embodiment of the present invention, there is no need to subject the solid stream to milling process. As a result, the process of the present invention is simple, more efficient requiring less equipment for carrying out the process with no hold time in view of faster/quicker dissolution of the solids in the suspension.

The advantages of the present invention include, without limitation:
- it aids in reducing particle size of the solids in a suspension by micronization;
- increases or enhances the dissolution kinetics and solubility of low soluble solids, such as APIs and excipients.
- enables increase in temperature during micronization process without the need for any external heat energy source;
- enables an efficient process as no additional batch operation is required to prepare the spray solution;

provides a process in which batch size is not limited by the feed tank capacity;

low or no hold time between solution preparation and spray drying eliminating potential spray solution stability issues associated, particularly in relation to low soluble solids such as drug active material and excipients;

provides continuous preparation of a spray solution;

provides a continuous method of preparing solid particles;

provides a method which is easily scalable.

The present disclosure provides a process for continuous drying a spray solution wherein said spray solution is formed by feeding at least one solid active pharmaceutical ingredient and/or at least one pharmaceutical excipient to at least one solvent forming a spray suspension that is fed to a micro-reactors or micro-channels system and continuously form a spray solution that is continuously fed to a nozzle that disperses said spray solution into droplets inside a drying chamber where a drying gas evaporates the solvents from each droplet forming solid particles that are collected on a cyclone.

Disclosed herein is a method for manufacturing single component particles and/or multi-component particles comprising the steps of:

Mixing, in a continuous or discontinuous mode, of at least one active pharmaceutical ingredient with at least one solvent, alone or along with one or more excipients to form a suspension;

Continuous feeding of said suspension to an intensifier pump which in turn continuously feeds the suspension to at least one micro-reactor and/or at least one micro-chamber;

High energy mixing of said suspension in said micro-reactor(s) and/or micro-chamber(s) by means of micro-reaction or microfluidization to produce a homogeneous spray solution stream;

Continuous feeding of said spray solution to a spray dryer;

Atomizing the said spray solution stream using at least one atomization nozzle to produce droplets stream;

Drying the said droplets stream in the drying chamber to obtain solid particles; and Collecting said solid particles.

The present invention also provides a system for continuous preparation of solid particles.

The present invention also provides for a process for continuous preparation of solid particles using the system of the present invention. The present invention also provides a product obtained by the process for continuous preparation of solid particles using the system of the present invention.

Preferably, in the present invention only one stream of suspension is used and is continuously fed to a spray-dryer to obtain a solid material in the end of the process.

The present invention also provides a pharmaceutical composition comprising the solid particles obtained by the process of the present invention using the system according to the present invention. The pharmaceutical composition is used as a medicine. Preferably the solid particles comprises single component particles, multi-component particles in amorphous or crystalline form (co-crystals) and amorphous solid dispersions, preferably having particle sizes in the micro- and/or nano-range.

The present invention also provides use of at least one microreactor and/or at least one micro-chamber for micronization of particles in a suspension comprising at least one component and at least one solvent in a process for the continuous manufacture of single component particles and/or multi-component particles. The at least one component may be an active pharmaceutical ingredient and/or an excipient having poor stability in solution, low solubility and/or low dissolution kinetics properties.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

EXAMPLES

Suitable examples, which are meant only to suggest a method of practicing the present invention and do not serve to limit the scope of the present invention, follows:

Example 1

Polyvinylpyrrolidone vinyl acetate (PVP/VA, 11.9 g) was added to water (467.3 g) at room temperature in a buffer tank under stirring to prepare a suspension with 2.5% w/w solids load. The resulting suspension was continuously passed through a series of five micro-reactors with microchannels having 500 micron diameter by means of an intensifier pump (MicroDeBEE) at a pressure of 1862 bar. After one single passage of the suspension through the series of five micro-reactors a homogeneous solution was obtained.

For comparison purposes, a PVP/VA (5.0 g) was mixed with water (203.6 g) at room temperature in a stirred vessel. Complete dissolution of PVP/VA was achieved after 1 h12 m.

The same experiment was repeated with the same setup for other pharmaceutical excipients and solvents. Trihalose is crystalline form and was used as a model for crystalline molecules to mimic API's. The obtained results are summarized in the Table 1 below.

TABLE I

| Formulation | | Continuous solution preparation | | | | Stirred tank dissolution at room temperature | | | |
| --- | --- | --- | --- | --- | --- | --- | --- | --- | --- |
| | | | | | | | | | time for |
| Solid | Solvent | Solids (g) | Solvent (g) | Concentration (% wt) | Continuous dissolution | Solid (g) | Solvent (g) | Concentration (% wt) | dissolution (hh:mm) |
| PVP/VA | Water | 11.9 | 467.3 | 2.5 | YES | 5.0 | 203.6 | 2.4 | 01:12 |
| | Ethanol | 4.25 | 180.2 | 2.4 | YES | — | — | — | Not tested |
| | Ethanol | 7.95 | 181.1 | 4.2 | YES | — | — | — | Not tested |

TABLE I-continued

| Formulation | | Continuous solution preparation | | | | Stirred tank dissolution at room temperature | | | |
| --- | --- | --- | --- | --- | --- | --- | --- | --- | --- |
| | | Solids | Solvent | Concentration | Continuous | Solid | Solvent | Concentration | time for dissolution |
| Solid | Solvent | (g) | (g) | (% wt) | dissolution | (g) | (g) | (% wt) | (hh:mm) |
| Poloxamer 188 | Ethanol | 10.55 | 411.6 | 2.5 | YES | 5.12 | 200.5 | 2.5 | 00:06 |
| | Ethanol | 13.67 | 333.8 | 3.9 | YES | — | — | — | Not tested |
| L-Leucine | H2O | 1.38 | 451.2 | 0.3 | YES | 1.34 | 461.3 | 0.3 | 00:48 |
| L-Leucine + Trehalose | H2O | 1.58 + 3.42 | 450 | 1.1% (32% L-Leuc + 68% Trehalose) | YES | 0.71 + 1.65 | 203.2 | 1.1 | 00:10 |

It can be seen from test results that dissolution of the solid particles takes place immediately or within few seconds (i.e. continuous dissolution) in the continuous solution preparation of the present invention whereas in the stirred tank dissolution as per the state-of-the-art the time taken for dissolution of particles range from 10 minutes to 1.12 hrs. Thus, the test results demonstrate that spray solution can be prepared continuously by the process of the present invention, in a time period of few seconds. When compared to stirred vessel dissolution, the increase in the dissolution kinetics may be explained as a result of micronization and high shear mixing effects inside the micro-reactors.

The invention claimed is:

1. A process for the continuous manufacture of amorphous solid dispersions or API alone particles comprising the steps of:
   continuously feeding a suspension comprising at least one component and at least one solvent to at least one microfluidization device;
   mixing the suspension in the microfluidization device by means of micro-reaction or microfluidization to produce a homogeneous spray solution;
   feeding said spray solution in a continuous mode to a spray dryer;
   atomizing said spray solution to produce droplets using at least one atomization nozzle; and
   drying said droplets in a drying chamber to obtain particles.

2. The process according to claim 1, wherein the suspension is prepared by mixing in a continuous or discontinuous mode at least one component with at least one solvent.

3. The process according to claim 1, wherein the at least one component comprises at least one active pharmaceutical ingredient (API), at least one excipient, or a combination of an API and an excipient.

4. The process according to claim 3, wherein the active pharmaceutical ingredient and/or the excipient has low solubility, low dissolution kinetics or poor stability in solution.

5. The process according to claim 3, wherein the at least one excipient is selected from the group consisting of: polymers, surfactants, sugars, amino acids, chitin, chitosan, alginates, polysaccharides, and combinations thereof.

6. The process according to claim 1, wherein the solvent is selected from the group comprising: water, methanol, ethanol, propanol, acetone, butanone, tetrahydrofuran, dichloromethane, hexane, DMSO, ethyl acetate, n-heptane and combinations thereof.

7. The process according to claim 1, wherein the microfluidization is effected using at least one microreactor and/or at least one micro-chamber.

8. The process according to claim 1, wherein the microfluidization is effected using at least one microreactor and/or at least one micro-chamber, which operates in a recirculation mode.

9. The process according to claim 7, wherein the microreactor is a continuous flow reactor.

10. The process according to claim 7, wherein the at least one microreactor or microchamber comprises one or more channels, optionally wherein the number of channels are in the range of about 1 to about 10.

11. The process according to claim 7, wherein the at least one microreactor or microchamber comprises one or more channels each having a diameter in the range of about 10 microns to about 1000 microns or in the range of about 50 microns to about 400 microns.

12. The process according to claim 1, wherein the microfluidization is effected using more than one microreactor, and wherein the microreactors are arranged in series or in parallel.

13. The process according to claim 12, wherein the number of microreactors arranged in series or in parallel ranges from about 1 to about 10.

14. The process according to claim 1, wherein the suspension comprising the component and the solvent is fed to the microreactor/microchamber using at least one pump, optionally wherein the pump comprises an intensifier pump.

15. The process according to claim 1, wherein the suspension is prepared by dispersing in a continuous or discontinuous mode at least one component in at least one solvent in a buffer tank and the suspension from the buffer tank is fed to the microreactor/microchamber using at least one pump, optionally wherein the pump comprises an intensifier pump.

16. The process according to claim 7, wherein the suspension is fed to the microreactor/microchamber at a pressure in range of about 1 bar to about 3500 bar or in the range of about from 1 to about 2000 bar.

17. The process according to claim 7, wherein the suspension comprising the component and the solvent is mixed in the one or more channels of microreactor/microchamber such that the particle size of the component is reduced by micronization.

18. The process according to claim 7, wherein the suspension comprising the component and the solvent is mixed in the one or more channels of microreactor/microchamber such that heat is generated.

19. The process according to claim 1, wherein said spray solution from the microfluidization device is delivered to a buffer tank.

20. The process according to claim 1, wherein said spray solution from the microfluidization device is recirculated to a first buffer tank in which a stream comprising the at least one component and a stream comprising the at least one solvent are combined.

21. The process according to claim 20, wherein the solution from the first buffer tank is transported to a second buffer tank, optionally wherein the solution from the second buffer tank is continuously fed to the spray dryer.

22. The process according to claim 1, wherein said spray solution is continuously fed to the spray dryer using at least one pump, optionally wherein the pump comprises an intensifier pump.

23. The process according to claim 1, wherein the at least one atomization nozzle is selected from the group comprising: a two fluid nozzle, a pressure nozzle, a rotary nozzle, an ultrasonic nozzle and combinations thereof.

24. The process according to claim 1, wherein the droplets formed from the spray solution ranges from about 1 to 200 μm, preferably in the range of about from 30 to 80 μm.

25. The process according to claim 1, wherein the spray solution is fed to said atomization nozzle at a hydrodynamic pressure in the range of from about 1 to about 200 bar or in the range of 10 to about 100 bar.

26. The process according to claim 1, wherein the droplets are dried in the drying chamber using a gas, optionally the gas comprises nitrogen, air, carbon dioxide or a combination thereof.

27. The process according to claim 1, wherein the drying gas when entering the drying chamber has a temperature in the range of from about −20 to about 200° C. or in the range of from about −10 to about 100° C.

28. The process according to claim 1, wherein the temperature of the drying gas exiting the drying chamber is lower than the temperature of the gas when entering the drying chamber.

29. The process according to claim 1, wherein the drying gas is recycled to the drying chamber after passing through a condenser.

30. The process according to claim 1, further comprising drying the spray dried particles in a secondary drying discontinuous operation, wherein optionally the secondary drying discontinuous operation includes: reducing pressure below room pressure, heating above room temperature or agitation.

31. The process according to claim 3, wherein the at least one excipient is a cellulosic polysaccharide or derivatives thereof.

32. The process according to claim 3, wherein the at least one excipient is a polymer with a vinyl group or a polymer with an acrylic or derivatives thereof.

33. The process according to claim 32, wherein the polymer with the vinyl group comprises poly vinyl pirrolidone, or wherein the polymer with the acrylic or derivatives thereof comprises poly methyl acrylic.

* * * * *